(12) United States Patent
Aggerholm et al.

(10) Patent No.: US 9,339,291 B2
(45) Date of Patent: May 17, 2016

(54) CUTTING OR SCORING BALLOON, SYSTEM AND METHOD OF MAKING A CUTTING OR SCORING BALLOON

(75) Inventors: Steen Aggerholm, St. Heddinge (DK); Per Erik Elgaard, Haslev (DK); Thomas Lysgaard, Solroed Strand (DK)

(73) Assignee: Cook Medical Technologies LLC, Bloomington, IN (US)

( * ) Notice: Subject to any disclaimer, the term of this patent is extended or adjusted under 35 U.S.C. 154(b) by 967 days.

(21) Appl. No.: 12/964,055

(22) Filed: Dec. 9, 2010

(65) Prior Publication Data

US 2011/0160756 A1    Jun. 30, 2011

Related U.S. Application Data

(60) Provisional application No. 61/290,536, filed on Dec. 29, 2009, provisional application No. 61/352,180, filed on Jun. 7, 2010.

(51) Int. Cl.
| | |
|---|---|
| A61B 17/22 | (2006.01) |
| A61B 17/3207 | (2006.01) |
| B29C 59/02 | (2006.01) |
| A61M 25/10 | (2013.01) |
| B29C 59/00 | (2006.01) |

(52) U.S. Cl.
CPC ....... *A61B 17/320725* (2013.01); *B29C 59/021* (2013.01); *A61B 2017/22061* (2013.01); *A61M 25/1027* (2013.01); *A61M 2025/1031* (2013.01); *B29C 59/007* (2013.01)

(58) Field of Classification Search
CPC ................... A61B 17/3207; A61B 17/320725
USPC ............. 606/159, 191–198; 604/103, 103.01, 604/103.06, 103.08
See application file for complete search history.

(56) References Cited

U.S. PATENT DOCUMENTS

| | | | |
|---|---|---|---|
| 5,620,418 A | 4/1997 | O'Neill et al. | |
| 5,693,014 A | 12/1997 | Abele et al. | |
| 6,264,633 B1 | 7/2001 | Knorig | |
| 7,303,572 B2 | 12/2007 | Melsheimer et al. | |

(Continued)

FOREIGN PATENT DOCUMENTS

EP    0204218    8/1989

OTHER PUBLICATIONS

PCT/US2010/059613 International Search Report May 25, 2011.

(Continued)

*Primary Examiner* — Tuan V Nguyen
(74) *Attorney, Agent, or Firm* — Richard J. Godlewski (57) ABSTRACT

A cutting or scoring balloon (10) of elongate shape and provided at its periphery with a plurality of scoring elements (12) extending longitudinally along the balloon. The scoring elements (12) are formed integrally with the balloon wall (14) and in the preferred embodiment are of the same material. A raw material form (20) for producing the balloon (10) is provided with a series of zones (26, 28) of greater thickness compared to the remainder of the balloon wall (24). These zones (26, 28) are located adjacent respective ribs (22) and extend longitudinally along the balloon wall for substantially the same distance as the ribs (22). The zones (26, 28) ensure that these will expand (stretch) preferentially compared to the remainder of the raw material form (20) and in particular the ribs (22), with the effect that the ribs (22) will not tend to be stretched.

21 Claims, 4 Drawing Sheets

(56) References Cited

U.S. PATENT DOCUMENTS

| | | | |
|---|---|---|---|
| 8,034,066 B2 * | 10/2011 | Goeken et al. | 606/159 |
| 2003/0144683 A1 | 7/2003 | Sirhan et al. | |
| 2005/0015107 A1 | 1/2005 | O'Brien | |
| 2005/0038383 A1 | 2/2005 | Kelley et al. | |
| 2005/0137615 A1 | 6/2005 | Mapes et al. | |
| 2005/0149082 A1 | 7/2005 | Yee et al. | |

OTHER PUBLICATIONS

PCT/US2010/059613 Written Opinion May 25, 2011.

* cited by examiner

CUTTING OR SCORING BALLOON, SYSTEM AND METHOD OF MAKING A CUTTING OR SCORING BALLOON

CROSS REFERENCE TO RELATED APPLICATIONS

This application claims the benefit of 61/290,536 filed on Dec. 29, 2009 entitled "CUTTING OR SCORING BALLOON, SYSTEM AND METHOD OF MAKING A CUTTING OR SCORING BALLOON" and application Ser. No. 61/352,180 filed on Jun. 7, 2010 entitled "CUTTING OR SCORING BALLOON, SYSTEM AND METHOD OF MAKING A CUTTING OR SCORING BALLOON" the entire contents of which are incorporated herein by reference.

TECHNICAL FIELD

The present invention relates generally to medical devices and more particularly to angioplasty balloon catheters used to dilate narrowed portions of a lumen such as by cutting or scoring balloons.

BACKGROUND ART

Balloon catheters are widely used in the medical profession for various intraluminal procedures. One common procedure involving the use of a balloon catheter relates to angioplasty dilation of coronary or other arteries suffering from stenosis (that is, a narrowing of the arterial lumen that restricts blood flow).

Although balloon catheters are used in many other procedures as well, coronary angioplasty using a balloon catheter has become particularly attractive to the medical community because of the growing number of people suffering from heart problems associated with stenosis. This has led to an increased demand for medical procedures to treat such problems. The widespread frequency of heart problems may be due to a number of societal changes, including the tendency of people to exercise less while eating greater quantities of unhealthy foods, in conjunction with the fact that people generally now have longer life spans than previous generations. Angioplasty procedures have become a popular alternative for treating coronary stenosis because angioplasty procedures are considerably less invasive than other alternatives. For example, stenosis of the coronary arteries has traditionally been treated with bypass surgery. In general, bypass surgery involves splitting the chest bone to open the chest cavity and grafting a replacement vessel onto the heart to bypass the blocked, or stenosed, artery. However, coronary bypass surgery is a very invasive procedure that is risky and requires a long recovery time for the patient.

To address the increased need for coronary artery treatments, the medical community has turned to angioplasty procedures, in combination with stenting procedures, to avoid the problems associated with traditional bypass surgery. Typically, angioplasty procedures are performed using a balloon-tipped catheter that may or may not have a stent mounted on the balloon (also referred to as a stented catheter). The physician performs the angioplasty procedure by introducing the balloon catheter into a peripheral artery (commonly one of the leg arteries) and threading the catheter to the narrowed part of the coronary artery to be treated. During this stage, the balloon is uninflated and collapsed onto the shaft of the catheter in order to present a low profile which may be passed through the arterial lumens. Once the balloon is positioned at the narrowed part of the artery, the balloon is expanded by pumping a mixture of saline and contrast solution through the catheter to the balloon. As a result, the balloon presses against the inner wall of the artery to dilate it. If a stent is mounted on the balloon, the balloon inflation also serves to expand the stent and implant it within the artery. After the artery is dilated, the balloon is deflated so that it once again collapses onto the shaft of the catheter. The balloon-tipped catheter is then retracted from the body. If a stent is mounted on the balloon of the catheter, the stent is left permanently implanted in its expanded state at the desired location in the artery to provide a support structure that prevents the artery from collapsing back to its pre-dilated condition. On the other hand, if the balloon catheter is not adapted for delivery of a stent, either a balloon-expandable stent or a self-expandable stent may be implanted in the dilated region in a follow-up procedure. Although the treatment of stenosed coronary arteries is one common example where balloon catheters have been used, this is only one example of how balloon catheters may be used and many other uses are also possible.

One problem that may be encountered with conventional angioplasty techniques is the proper dilation of stenosed regions that are hardened and/or have become calcified. Stenosed regions may become hardened for a variety of reasons, such as the build-up of artherosclerotic plaque or other substances. Hardened regions of stenosis can be difficult to completely dilate using conventional balloons because hardened regions tend to resist the expansion pressures applied by conventional balloon catheters.

It is also known to use cutting or scoring balloons in order to cut away at plaque and other build-up on the interior walls of a lumen. Examples can be found in the applicant's own earlier U.S. Pat. No. 7,303,572, as well as in U.S. Pat. No. 5,620,418 and US-2005/0137615. Cutting balloons can be a very effective way to remove plaque and other build-up in a vessel via an endoluminal procedure, particularly in conjunction with a filter for trapping the removed material. They provide a rapid and effective medical procedure with few or none of the side effects of open surgery procedures of the type highlighted above.

There are problems, however, with such cutting balloons, particularly related to their manufacture. Some forms of cutting balloon provide for the fixing onto the surface of the balloon of cutting elements, such as blades. This is a laborious process which furthermore results in a cutting balloon with limited compressibility, making it unsuitable for some medical applications.

Other forms of cutting balloon mould cutting protrusions into the surface of the balloon. However, heretofore this has not been an entirely successful task for several reasons. First, balloon catheters are stretched by inflation during manufacture as well as during use, with the result that surface irregularities including protrusions in the material tend to stretch and thus flatten. Attempts to solve this problem by making the protrusions of thicker material do not resolve the problem entirely and also add bulk to the balloon catheter and thus hinder its compressibility.

DISCLOSURE OF THE INVENTION

The present invention seeks to provide an improved cutting or scoring balloon as well as an improved system for and method of manufacturing a cutting or scoring balloon. In what follows, the term scoring balloon is used to denote a cutting or a scoring balloon, that is a balloon able to cut or score through plaque and other build-up within a patient's lumen.

According to an aspect of the present invention, there is provided a scoring balloon raw material form for an angioplasty balloon catheter including a balloon wall, and one or more scoring elements formed integrally with the balloon wall; wherein the balloon wall includes at least one zone of increased thickness adjacent the or each scoring element.

According to another aspect of the present invention, there is provided a scoring balloon for an angioplasty balloon catheter including a balloon wall, and one or more scoring elements formed integrally with the balloon wall; wherein the balloon wall is formed with at least one zone of increased thickness adjacent the or each scoring element.

The provision of a thicker part to the balloon wall at the region of the or each scoring element causes the thicker part of the balloon wall to stretch differentially compared to the remainder and thinner of the balloon wall and thus reduces or avoids any stretching and thus flattening of the scoring element or elements. This can also avoid the need to have scoring elements which are otherwise unnecessarily thickened to withstand manufacturing and usage stretching and thus can lead to a balloon catheter with a smaller collapsed profile than prior art devices.

The or each scoring element may have a concave inner surface, in some embodiments an inner surface comparable to the outer surface thereof. In other words, the or each scoring element does not need to be of a solid volume but can be at least partially hollow in the interior thereof. This has the advantage that the scoring elements have a smaller volume thus enabling the balloon to collapse to a smaller size than prior art scoring or cutting balloons.

Advantageously, the balloon wall either side of a cutting or scoring element includes a portion of greater thickness compared to the remainder of the balloon walls. Such a feature can ensure substantially less, preferably substantially no, stretching of the balloon at the regions of increased wall thickness compared to other regions of the balloon. This can ensure there is substantially no effective flattening of the cutting or scoring elements during inflation of the balloon.

In the preferred embodiment, the balloon has a wall which is generally and substantially of even thickness, one or more scoring elements formed in the balloon wall, each scoring element being sandwiched between zones of increased balloon wall thickness. Advantageously, the various parts to the scoring balloon are manufactured from the same materials, which can significantly simplify the manufacturing process. It is envisaged, however, that the scoring element or elements could be formed from a material different from that of the remainder of the balloon wall, such as from a stiffer material.

The or each scoring element may extend in a longitudinal direction of the scoring balloon. In another embodiment, the or each scoring element extends both longitudinally along and circumferentially around the balloon, such as helically. It is also envisaged that the or each scoring element could extend solely circumferentially around the balloon.

In some embodiments the scoring element or elements extend for a substantial length of the balloon, such as for substantially the entire of the widest part of the balloon when inflated. In other embodiments, the scoring balloon or balloons may extend for only a part of the length of the balloon and could be considered "short". There may even be a plurality of scoring elements arranged substantially linearly along the length of the scoring balloon, that is in a linear array or in a slightly overlapping array.

In the preferred embodiment the or each scoring element has a pointed apex. Advantageously, the or each scoring element is substantially triangular in transverse cross-section. A triangular scoring element can be more readily folded closed, while providing a very effective scoring or cutting function.

In addition to the advantages mentioned above, the preferred embodiment can be made of a common material and/or in a common manufacturing procedure, thus considerably facilitating the manufacturing process.

The present invention also provides a balloon catheter including a scoring balloon as herein specified.

According to another aspect of the present invention, there is provided apparatus for manufacturing a scoring balloon, which scoring balloon includes at least one scoring element; the apparatus including an expansion unit for expanding a raw material form, the expansion unit including a chamber for receiving a said raw material form; an inflation unit operable to inflate the raw material form to produce a catheter balloon; at least one scoring element support operable to support the or each scoring element upon inflation of the raw material form.

The scoring element support has the function to prevent undesired deformation of the or each scoring element during the process of expanding the raw material form, thereby minimising or avoiding loss of effectiveness of the scoring elements of the type experienced by prior art systems.

Advantageously, the at least one scoring element support is arranged to be movable within the expansion unit, thereby to move with the scoring element or elements as the raw material form is inflated. Thus, the scoring elements can be supported for a significant part of the balloon forming process.

For this purpose, the or each scoring element support may be in the form of a slidable guide having a channel or recess therein able to support the apex of the or each scoring element and biased towards the raw material form by, for example, a sprung element. Such scoring element supports provide a support to the apex or point of the scoring elements as the raw material form is inflated to produce the final balloon, assisting in ensuring that these do not become blunt during the formation process.

Preferably, the channel or recess in the or each scoring element support has a form which is complementary to the walls of the or each scoring element, thereby encapsulating at least a part of these adjacent the scoring tip. So doing can ensure that the scoring elements do not splay outwardly during the inflation of the raw material form.

BRIEF DESCRIPTION OF THE DRAWINGS

Embodiments of the present invention are described below, by way of example only, with reference to the accompanying drawings, in which.

DESCRIPTION OF THE PREFERRED EMBODIMENTS

It is to be understood that the drawings do not show the components to scale. In many instances dimensions are exaggerated in the drawings in order to show more clearly one or more features of the preferred embodiments.

Figure 1:
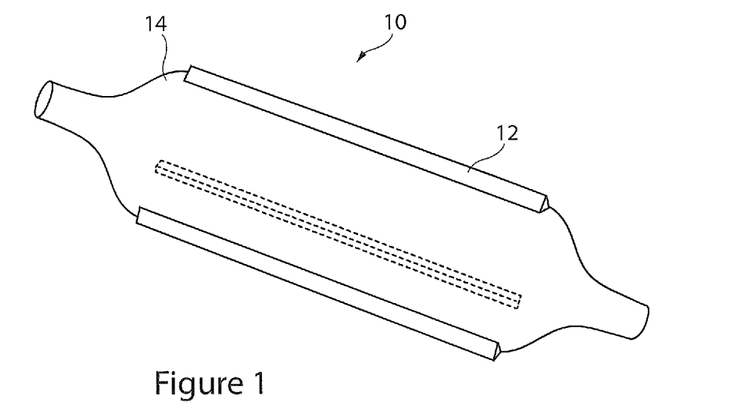
FIG. 1 is a perspective view of an embodiment of scoring or cutting balloon of the type taught herein.

Referring first to FIG. 1, there is shown a perspective view in schematic form of an embodiment of cutting or scoring balloon 10 of elongate shape and provided at its periphery with a plurality of scoring or cutting elements 12 extending longitudinally along the balloon. The scoring elements 12 are formed integrally with the balloon wall 14 and in the preferred embodiment are of the same material.

There are preferably provided a plurality of such scoring elements 12, advantageously spaced substantially evenly around the circumference of the balloon 10. In the embodiments which follow there are provided three scoring elements 12, although the number of these will be dependent upon the particular application and wishes of the user/designer.

FIG. 1 shows the scoring elements 12 extending for the substantial length of the balloon 10. In some embodiments the scoring elements 12 may be considerably shorter, for example to extend for less than 50% of the length of the balloon. Furthermore, in some embodiments, each scoring element 12 may be formed of a plurality of shorter element sections aligned in series with respect to one another. Such an arrangement can provide the balloon 10 with greater longitudinal flexibility particularly for use in a curved lumen.

The balloon 10 and the scoring elements 12 can be made of any of the known materials for such devices and preferably of a substantially non-compliant material. Examples of balloon material include Nylon, preferably Nylon 12, Pebax, PET, PE, PU and similar materials, and furthermore also including co-extrusions and blends of more than one of these materials.

The scoring balloon 10 of FIG. 1 can be used in the same manner as known cutting and scoring balloons, typically on the end of a catheter which provides an inflation function for inflating the balloon 10 within a patient's lumen. The scoring balloon 10 can then be rotated to score into and thus cut away plaque and other deposits on the inside wall of the lumen, which fragments can be collected by a suitable filtration device or mechanism. Following use, the balloon 10 can be deflated again so that it can be removed from the patient. This type of angioplasty operation is well known to the skilled person so is not described in further detail herein.

Figure 2:
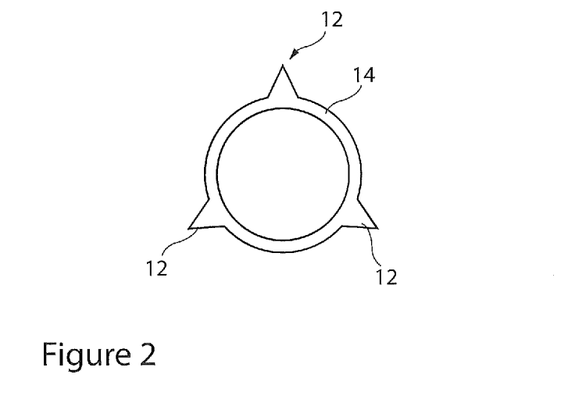
FIG. 2 is a view in transverse cross-section of an embodiment of scoring or cutting balloon.

Referring now to FIG. 2, there is shown, in schematic form, a transverse cross-sectional view of an embodiment of scoring balloon provided with three scoring elements 12. Each element 12 preferably has a triangular shape when viewed in transverse cross-section, with an apex pointing substantially radially from the centre of the scoring balloon 10. Each element 12 is also an integral part of the balloon wall 14 and preferably formed of the same material and at the same time as the balloon wall 14, as described in further detail below. In use, the scoring elements 12 provide a relatively sharp or hard point for use in scoring and thus scoring away at plaque or other deposits on the internal surfaces of a patient's stenosed lumen.

Figure 3:
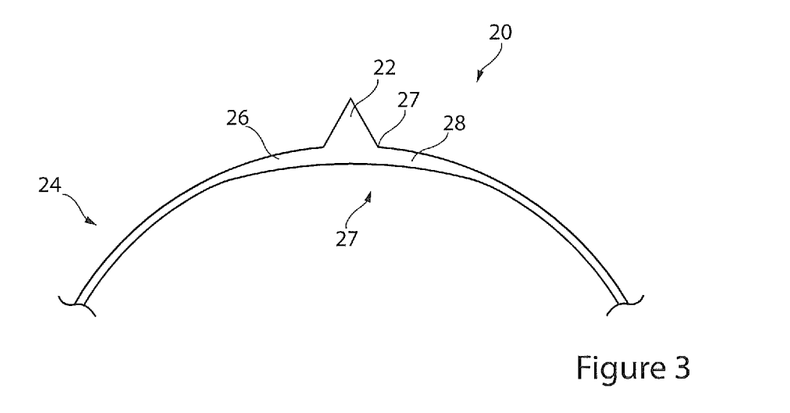
FIG. 3 is a view in transverse cross-section of an embodiment of raw material form for producing the balloon of FIG. 2.

FIG. 3 shows an embodiment of raw material form for producing a balloon having the features of FIGS. 1 and 2. The raw material form 20 is an extruded component having the transverse cross-sectional form shown in the drawing and is typically the penultimate stage in the manufacture of the balloon 10. The raw material form 20 is subsequently expanded by inflation to produce the final the balloon 10, as described below. Such expansion is typically a substantially plastic expansion carried out under a relatively high heat. As the raw material form 20 is simply inflated to create the balloon 10 it has a very similar structure to that of the final balloon, with in the preferred embodiment a notable exception. The raw material form thus has a long shape which is generally round in transverse cross-section, as can be seen in FIG. 3. Preformed within its wall 24 are a plurality of elongate pointed ribs 22 which will form the scoring elements 12.

Whereas the wall 14 of the balloon 10 is generally of even thickness, in the raw material form 20 the wall 24 is provided with a series of zones 26, 28 of greater thickness compared to the remainder of the balloon wall 24. These zones 26, 28 are located adjacent respective ribs 22 and extend longitudinally along the balloon wall for substantially the same distance as the ribs 22. As can be seen in FIG. 3, the zones 26, 28 are located on opposite sides of an adjacent rib 22. In one embodiment, the zones 26, 28 have a thickness which is comparable to that of the wall 14 of the finished balloon 10 so that once formed the balloon 10 will have walls which are substantially evenly thick throughout their circumference. This is not essential, though, as it is envisaged also that these zones 26, 28 could remain thicker relative to the remainder of the balloon wall 24. As in practice the portions 26, 28 would typically have a smooth profile, they would not impinge upon the operation or characteristics of the balloon 10 and in some instances could actually contribute to the efficacy of the cutting or scoring elements 12 by providing to these a more solid base which would have the effect of increasing the cutting or scoring pressure which can be applied by the elements 12.

The provision of zones 26, 28 of increased thickness ensures that these will expand (stretch) less compared to the remainder of the raw material form 20 and in particular the remainder of the wall 24, with the effect that the ribs 22 will not tend to be stretched anywhere near the extent to which they are stretched in existing cutting or scoring balloons. Thus, there is a markedly reduced incidence of flattening or blunting of the scoring elements 12 during manufacture. Not only does this improve the quality of the final device 10 but it also provides a simpler method of manufacture of a scoring balloon with integral scoring elements. More specifically, in cases where the scoring elements 12 may splay or stretch so as to become blunt during the balloon manufacturing stage, in particular during the stage in which the raw material form is expanded to produce the balloon itself, it may be necessary to effect a post-expansion treatment such as fitting scoring elements or otherwise sharpening the integral scoring elements. This can be inconvenient and costly.

In the preferred embodiment, the zones 26, 28 have a thickness of in the region of 100% to 600% greater than the thickness of the remainder of the wall 24, more preferably between 100% to 400% greater and most preferably 100% to 200% greater measured at the transition point between the balloon wall and the cutting or scoring element, identified as point or zone 27 in FIG. 3. Advantageously, each zone 26, 28 extends radially in the region of 10% to 20% of the overall circumference of the raw material form 20 (this depending of course on the number of the scoring elements 12 and the radial extent to which they encompass the balloon 10), more preferably between 10% to 15% of the circumference of the wall 24 and most preferably around 12% in the case of a balloon with four cutting or scoring elements. In the case of a balloon provided with four scoring elements, the region of each zone of increased thickness, that is the region including the cutting or scoring element 22 and the zones 26, 28 either side thereof, will preferably be in the range of 10° to 60°, more preferably in the range from 20° to 50° and in the preferred embodiment in the region of 30 to 40°. These angles could apply as well to balloons having a different number of cutting or scoring elements. The same may be the case once the balloon 10 has been fully formed for embodiments in which the zones 26, 28 remain thicker in the final balloon 10.

It will be appreciated that these proportions and parameters are suitable for the embodiment of scoring balloon shown in the drawings and that different designs and sizes of balloon, such as balloons having a different number of elements and larger balloons will have zones 26, 28 of different proportions and dimensions.

In connection with FIG. 3, it is envisaged that in some embodiments the zones 26 and 28 may be asymmetric. For instance, the zone 26 may be shorter than the zone 28, that is it may extend by a smaller radial extent compared to the zone 28.

Figure 4:
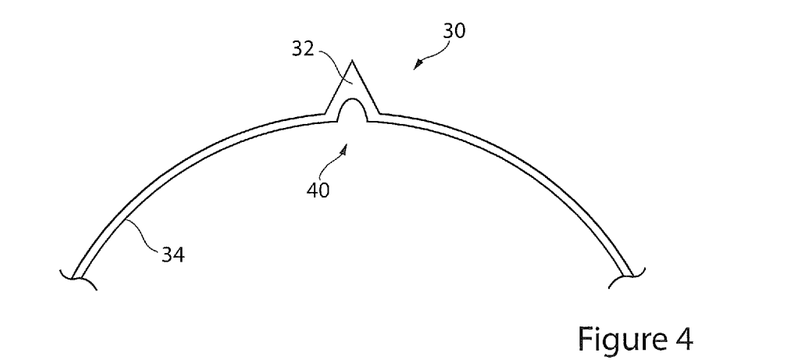
FIG. 4 is a view in transverse cross-section of another embodiment of raw material form for producing the balloon of FIG. 2.

FIG. 4 shows another embodiment of raw material form 30, in the drawing only a part of the raw material form being shown. The raw material form 30 has features similar to that of FIG. 3. It could, for instance, be provided with one or more zones of increased wall thickness such as the zones 26 and 28.

In this embodiment, the or each rib 32 is not of a solid construction as is the case, for example, with the rib 22 of FIG. 3 and the scoring elements 12 of the embodiment of FIGS. 1 and 2. By contrast, each rib 32 has a hollowed base, provided by an indent 40. The indent 40 still ensures that the thickness of the wall by the cutting or scoring element 32 is thicker than the balloon wall 34 to ensure differential stretching during inflation of the raw material form 30 and thus reduction or avoidance of flattening of the scoring elements.

Such an "indented" structure allows the balloon to be more flexible in compression, in that the ribs or scoring elements 32 are also able to compress to an extent during folding or wrapping of the balloon. This can be particularly advantageous for balloons of very small dimensions or which must be compressed particularly tightly for introduction into a patient's vasculature up to the deployment site.

It is also envisaged that the embodiment of FIG. 4 could also have zones of increased thickness either side of the cutting or scoring element 32, for example in the of bulges so as to have significantly greater thicknesses than the remainder of the balloon wall areas. Such zones can protect, by their greater strength, the ribs 32 during inflation of the balloon. It will be appreciated that this feature could also be used with ribs 22 which do not have indented bases.

It is not excluded, particularly in connection with the manufacturing device disclosed below, that the balloon could be formed with a substantially even wall thickness throughout its radial extent.

Figure 5A:
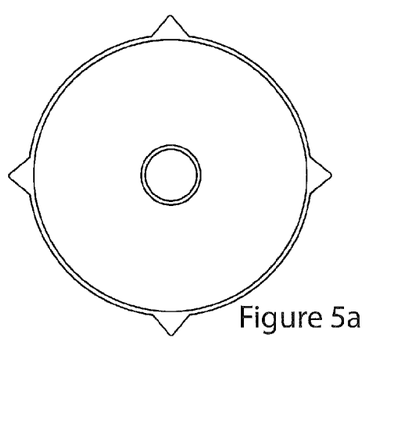
FIG. 5a shows an example of prior art scoring balloon in an inflated condition.
Figure 5B:
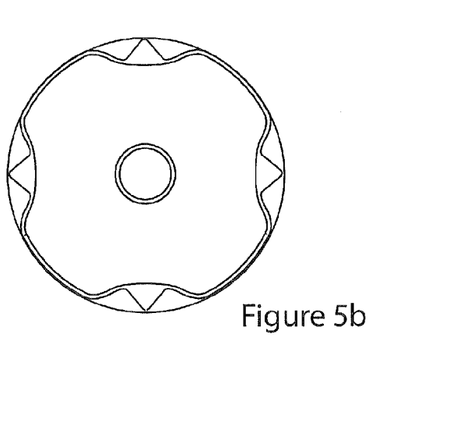
FIG. 5b shows the scoring balloon of FIG. 5a when compressed in a lumen.
Figure 6A:
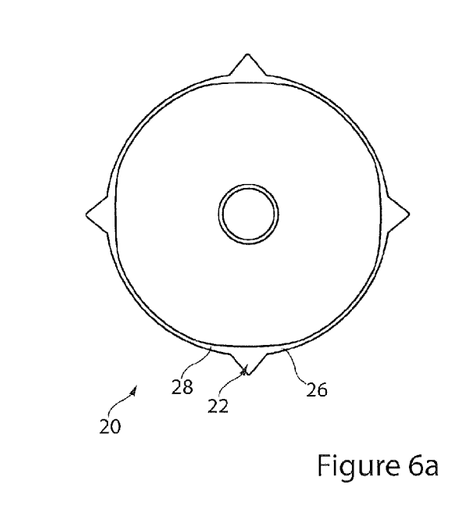
FIG. 6a shows an embodiment of scoring balloon according to the invention, in an inflated condition.
Figure 6B:
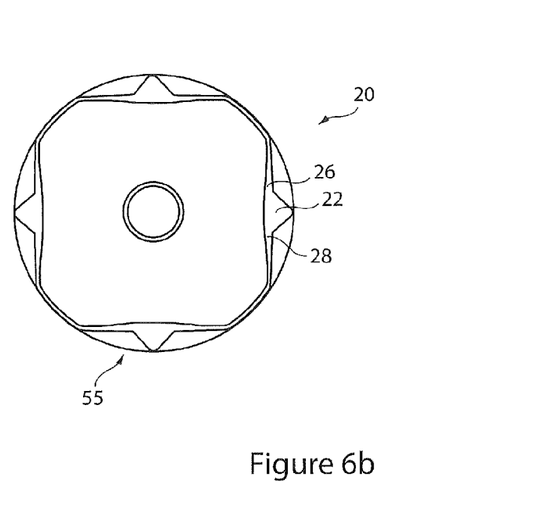
FIG. 6b shows the scoring balloon of FIG. 6a when compressed in a lumen.

The zones 26 and 28 of increased thickness provide a number of other advantages to this cutting or scoring balloon 20. A problem with existing designs of balloons of this nature is that the pliancy of the balloon reduces the effective force which is applied by the cutting and scoring elements against the stenosis of a lumen wall, causing the cutting or scoring elements to be pushed inwardly of the balloon and thus reducing their efficacy. A sharper cutting or scoring element may reduce this disadvantage but presents other disadvantages such as increased risk of damage to the balloon while it is wrapper and to the vessel walls. By contrast, the regions 26, 28 of increased thickness provide in effect a platform around the cutting or scoring element 22, which assists in pressing this against the lumen wall. This can significantly increase the performance of the device without the need to use sharper cutting or scoring elements. In fact, it has been found that the balloon 20 can work efficiently even with relatively blunt cutting or scoring elements 22. This is shown in FIGS. 5a, 5b, which show a prior art balloon structure, and FIGS. 6a and 6b, which show the balloon 20 in a lumen. As can be seen, the regions 26 and 28 of increased thickness assist in pressing the cutting or scoring elements 22 against the lumen wall 55.

Furthermore, the thinner regions of balloon wall can assist in the wrapping of the balloon 20 for deployment purposes. In this regard, it is preferred that the thinner wall sections are sufficiently narrow that when the balloon is wrapped, the cutting or scoring elements 22 are wrapped on the inside and the thinner parts folded and wrapped over these. Thus, the thinner parts of the balloon wall will not come into contact with the cutting or scoring elements 22.

Figure 7:
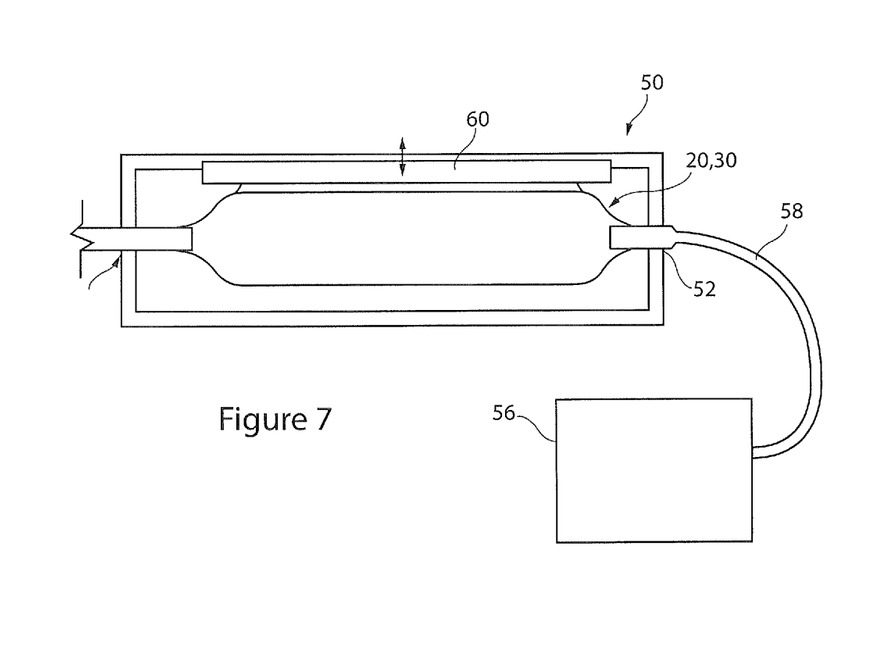
FIG. 7 is a schematic diagram of an embodiment of balloon forming apparatus.
Figure 8:
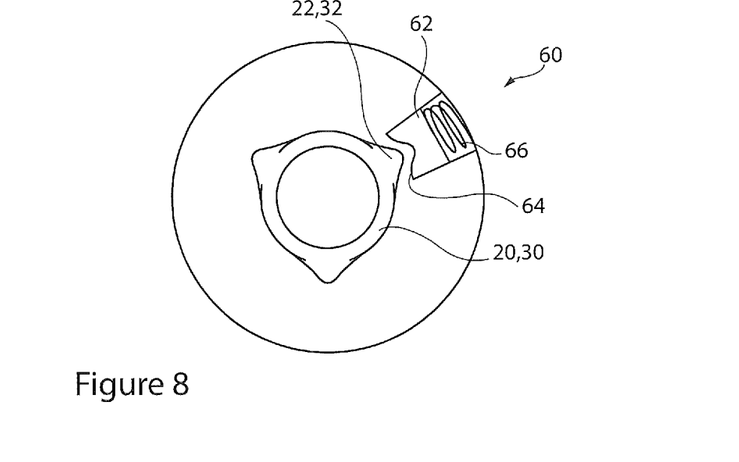
FIG. 8 is a front elevational view of a part of the apparatus of FIG. 7 showing in particular the reciprocably movable cutter element supports thereof.

Referring now to FIGS. 7 and 8, there is shown a preferred embodiment of apparatus for forming a balloon 10, which embodiment protects the shape of the scoring elements as the raw material form is inflated to create the final balloon.

FIG. 7 shows in schematic form a raw material form inflation device which includes a chamber 50 for holding the raw material form 20, 30 on fittings 52. A pumping and control unit 56 is provided for feeding pressurized air through a tube 58 to the interior of the raw material form 20, 30.

Within the casing 50 there is provided a series of scoring element supports 60 which are able to move reciprocably relative to the casing and arranged to move with the raw material form 20, 30 as this expands under the inflation pressure. The scoring element supports 60 are best seen in FIG. 8. They are preferably provided with an elongate body portion 62 having a longitudinally extending channel 64 therein having an opening wide enough to accommodate the apex of a rib 22, 32 of the raw material form 20, 30. The body portion 62 of each support is held within a suitable recess in the wall of the chamber 50 or in any other suitable holding element, by a spring 66 which biases the support 60 towards the raw material form, that is towards what could be said to be the central longitudinal axis of the casing 50. In this manner, it can be ensured that each support 60 is always trained onto the raw material form 20, 30 such that the apices of the ribs 22, 32 are always held within the channels 64.

It is preferred that the channels 64 are of such a shape and size that they can support at least an extent of the walls forming the ribs 22,32 so as to support these during the inflation procedure and thus to ensure that the ribs 22, 32 do not splay outwardly during this inflation process. In one embodiment, the channel 64 is able to accommodate at least 25% of the rib 22, 32, that is at least 25% of the extent of the two walls forming the ribs 22, 32, in some cases at least 50%. Preferably, the channels 64 are able to accommodate the entirety of the ribs 22, 32, for example having a depth which is substantially 1:1 in correspondence with the height of the cutting or scoring elements 12 of the balloon 10. Typically, the cutting or scoring elements 12 will have a height of 0.20 to 0.5 millimeters.

Thus, when a raw material form 20, 30 is fitted in the chamber 60, the supports 60 are allowed to spring onto the ribs 22, 32. As the raw material form 20, 30 is then inflated, the ribs 22,32 push against the supports 60, which are pressed outwardly to allow this expansion but do so while they support all the time the apices of the ribs 22, 32. This helps in preventing the splaying of the walls of the ribs 22, 32 and thus the flattening of the scoring elements 12 during the inflation process. Coupled with the provision of thinner wall zones either side of each rib 22, 32, the balloon can be inflated while retaining the efficacy and integrity of the integral scoring elements. Therefore, the system and balloon structure taught herein can provide a more effective cutting or scoring balloon and a simple and efficient manufacturing system and method for producing such a scoring balloon.

Although the preferred embodiments are shown with zones of greater thickness either side of the ribs 22, 32 of the raw material forms, this is not necessarily always the case. It is envisaged in some embodiments that there might be provided a single zone of greater thickness located at one side of a rib 22, 32, for example.

Apparatus according to claim 20, wherein the at least one scoring element support is arranged to be movable within the expansion unit, thereby to move with the scoring element or elements as the raw material form is inflated.

Apparatus according to claim 20, wherein the or each scoring element support is in the form of a slidable guide having a channel or recess therein able to support the apex of the or each scoring element and biased towards the raw material form.

Apparatus according to claim 22, wherein the channel or recess in the or each scoring element support has a form which is complementary to the walls of the or each scoring element.

What is claimed is:

1. A scoring balloon raw material form for an angioplasty balloon catheter including a balloon wall, and one or more scoring elements formed integrally with the balloon wall; wherein the balloon wall includes at least one zone of greater thickness adjacent the or each scoring element, the at least one zone of greater thickness extending radially in the region of 10% to 20% of the overall circumference of the raw material form.

2. A scoring balloon raw material form according to claim 1, wherein the at least one zone of greater thickness extends radially in the region of 10% to 15% off the circumference of the wall.

3. A scoring balloon raw material form according to claim 2, wherein the or each scoring element is substantially V-shaped in transverse cross-section.

4. A scoring balloon raw material form according to claim 1, wherein the raw material form has a wall which is generally and substantially of even thickness, one or more scoring elements formed in the balloon wall, each scoring element being sandwiched between zones of greater balloon wall thickness.

5. A scoring balloon raw material form according to claim 1, wherein the balloon wall and the scoring elements are formed of the same material.

6. A scoring balloon raw material form according to claim 1, wherein the at least one zone of greater thickness extends radially in the region of 12% of the circumference of the wall.

7. A scoring balloon raw material form according to claim 1, wherein the or each scoring element extends in a longitudinal direction of the scoring balloon.

8. A scoring balloon raw material form according to claim 7, wherein the scoring element or elements extend for a substantial length of the balloon.

9. A scoring balloon raw material form according to claim 7, wherein a plurality of scoring elements are arranged substantially linearly along the length of the scoring balloon.

10. A scoring balloon raw material form according to claim 1, wherein the or each scoring element has a pointed apex.

11. A scoring balloon raw material form according to claim 1, wherein the or each scoring element has a concave inner surface.

12. A scoring balloon for an angioplasty balloon catheter including a balloon wall, and one or more scoring elements formed integrally with the balloon wall; wherein the balloon wall is formed with at least one zone of greater thickness adjacent the or each scoring element, the at least one zone of greater thickness extending in an arc in the range of 10° to 60°.

13. A scoring balloon according to claim 12, wherein the at least one zone of greater thickness extends in an arc in the range of 20° to 50°.

14. A scoring balloon according to claim 12, wherein the or each scoring element has a concave inner surface.

15. A scoring balloon according to claim 14, wherein the or each scoring element is substantially V-shaped in transverse cross-section.

16. A scoring balloon according to claim 12, wherein the balloon has a wall which is generally and substantially of even thickness, one or more scoring elements formed in the balloon wall, each scoring element being sandwiched between zones of greater balloon wall thickness.

17. A scoring balloon according to claim 12, wherein the balloon wall and the scoring elements are formed of the same material.

18. A scoring balloon according to claim 12, wherein the scoring elements are integrally formed with the balloon.

19. A scoring balloon according to claim 12, wherein a plurality of scoring elements are arranged substantially linearly along the length of the scoring balloon.

20. A scoring balloon according to claim 12, wherein the or each scoring element has a pointed apex.

21. A scoring balloon for an angioplasty balloon catheter including a balloon wall, and one or more scoring elements formed integrally with the balloon wall; wherein the balloon wall is formed with at least one zone of greater thickness adjacent the or each scoring element, the at least one zone of greater thickness extending in an arc in the range of 30° to 40°.

* * * * *